US010022086B1

(12) United States Patent
Kahn et al.

(10) Patent No.: US 10,022,086 B1
(45) Date of Patent: Jul. 17, 2018

(54) EXTENDED BAND SYSTEM

(71) Applicants: Philippe Richard Kahn, Santa Cruz, CA (US); Arthur Kinsolving, Santa Cruz, CA (US); David Vogel, Santa Cruz, CA (US)

(72) Inventors: Philippe Richard Kahn, Santa Cruz, CA (US); Arthur Kinsolving, Santa Cruz, CA (US); David Vogel, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 53 days.

(21) Appl. No.: 14/255,923

(22) Filed: Apr. 17, 2014

Related U.S. Application Data

(60) Provisional application No. 61/814,178, filed on Apr. 19, 2013.

(51) Int. Cl.
*A61B 5/00* (2006.01)

(52) U.S. Cl.
CPC .......... *A61B 5/6802* (2013.01); *A61B 5/0022* (2013.01); *A61B 5/6887* (2013.01); *A61B 5/746* (2013.01); *A61B 5/747* (2013.01)

(58) Field of Classification Search
USPC ...................................................... 340/573.1
See application file for complete search history.

(56) References Cited

U.S. PATENT DOCUMENTS

| | | | | |
|---|---|---|---|---|
| 8,680,974 B2 * | 3/2014 | Meiertoberens | ..... | A61B 5/0002 340/12.5 |
| 8,738,925 B1 * | 5/2014 | Park | ......... | H04B 7/26 380/270 |
| 8,892,036 B1 * | 11/2014 | Causey | ............. | H04M 1/72516 455/41.2 |
| 8,942,719 B1 * | 1/2015 | Hyde | .................. | G01S 5/0231 455/411 |
| 2005/0075116 A1 * | 4/2005 | Laird | ....................... | A61B 5/04 455/456.3 |
| 2007/0251997 A1 * | 11/2007 | Brown | ................. | G06K 7/0008 235/380 |
| 2012/0083715 A1 * | 4/2012 | Yuen | .................... | A61B 5/0002 600/595 |
| 2013/0023214 A1 * | 1/2013 | Wang | .................. | A61B 5/0002 455/41.2 |
| 2014/0135955 A1 * | 5/2014 | Burroughs | .......... | G06F 19/3481 700/91 |
| 2015/0178362 A1 * | 6/2015 | Wheeler | ............. | G06F 9/44505 707/639 |
| 2015/0265903 A1 * | 9/2015 | Kolen | ............. | G06Q 10/06398 700/91 |

\* cited by examiner

*Primary Examiner* — Edward Urban
*Assistant Examiner* — Ralph H Justus
(74) *Attorney, Agent, or Firm* — HIPLegal LLP; Judith Szepesi

(57) ABSTRACT

A method and apparatus to provide an extended band is described. The method comprises pairing a body-worn device and a host device and establishing a low-power connection between the body-worn device and the host device to form an extended band. The method further comprises monitoring a user's status with a plurality of sensors on the host device and/or the body-worn device, and using the extended band to do one or more of: provide alerts to the user, based on the sensor data, control the extended band from one of the devices, and share data with third parties using the extended band.

21 Claims, 12 Drawing Sheets

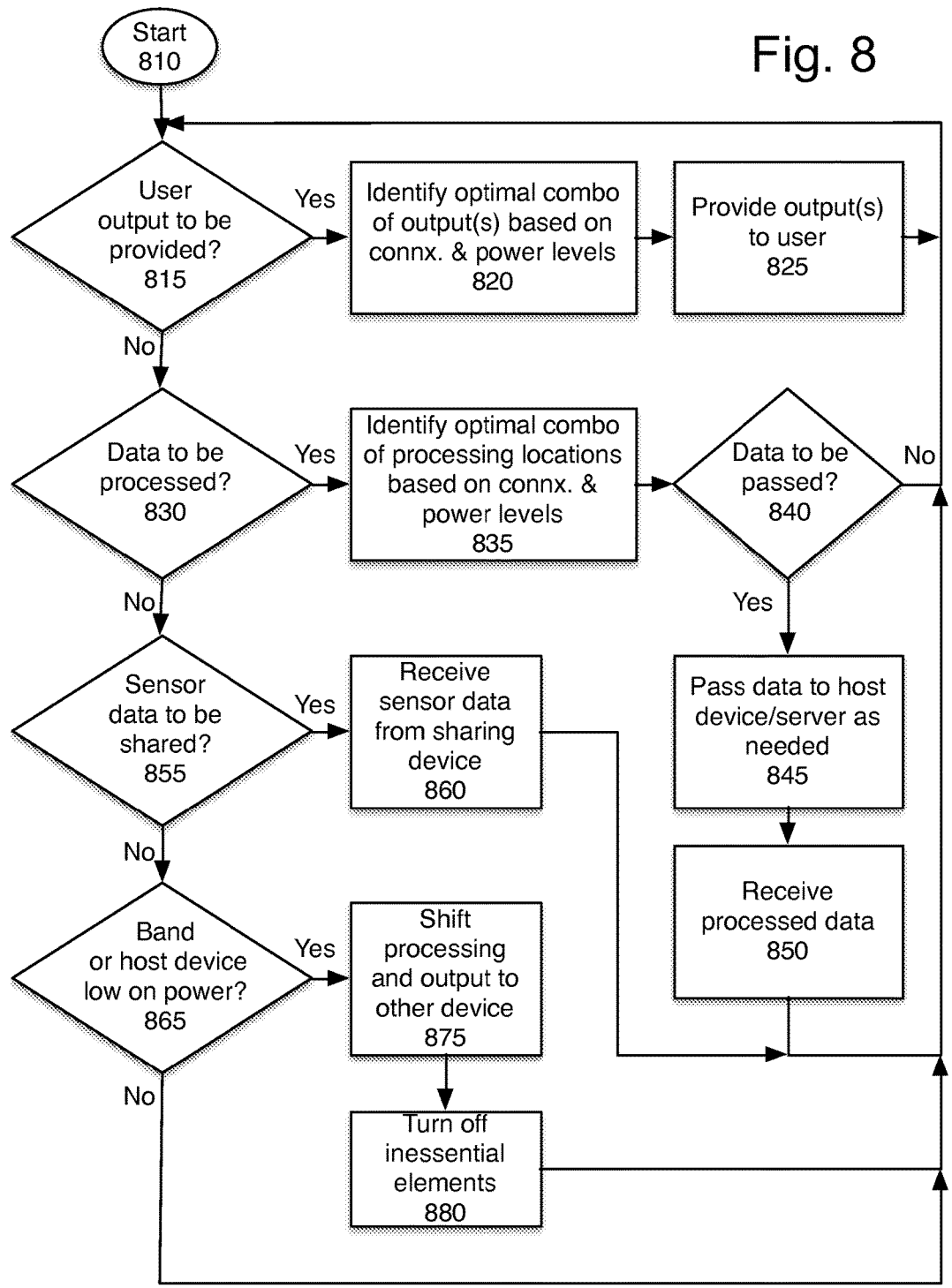

| | Band | Mobile Device |
|---|---|---|
| Get Active Alerts (inactivity alerts) | vibration | audible alert or text |
| Band's battery is low | LED color change | battery indicator flashing |
| Band's battery is fully charged | LED color change | battery indicator showing full |
| Timed steps recording started/in-progress/stopped | Flashing LEDs/step count | Chart of steps taken, and current status |
| Sleep session started/in-progress/stopped | Active v. sleep state indicator | Chart of sleep state status |
| PowerNap started/in-progress/stopped | Sleep state indicator, colored for power nap | Power nap display, with time count-down |
| Put band to sleep | Push button in pattern | Use visual menu/icon |
| Wake band up | Perform gesture command | use visual menu/icon |
| Waking up user | vibration | Audio alarm, optionally user's perferred music |
| Getting ready for sleep | LED, recommendation to fix environment | Home automation controls to ready space for sleep |
| Review of activity for the day | Display of total step count, or LED color | Chart showing activity level, goals, and status |

Fig. 9

EXTENDED BAND SYSTEM

RELATED APPLICATIONS

The present application claims priority to U.S. Provisional Application No. 61/814,178, filed on which is incorporated herein by reference.

FIELD

The present invention relates to a body-worn device, and more particularly to an extended body-worn device.

BACKGROUND

As accelerometers and other sensors are becoming more accurate, lower power, more cost-effective and smaller. There are numerous systems available, which enable a user to monitor his or her activity or sleep.

For example, there are pedometers or other activity monitors that track a user's activities to improve health. There are also some sleep monitors, which use accelerometers.

BRIEF DESCRIPTION OF THE FIGURES

The present invention is illustrated by way of example, and not by way of limitation, in the figures of the accompanying drawings and in which like reference numerals refer to similar elements and in which:

FIG. 8 is a flowchart of one embodiment of shared processing on the extended band.

FIG. 9 is a table of some exemplary inputs and outputs using the extended band.

DETAILED DESCRIPTION

Figure 1:
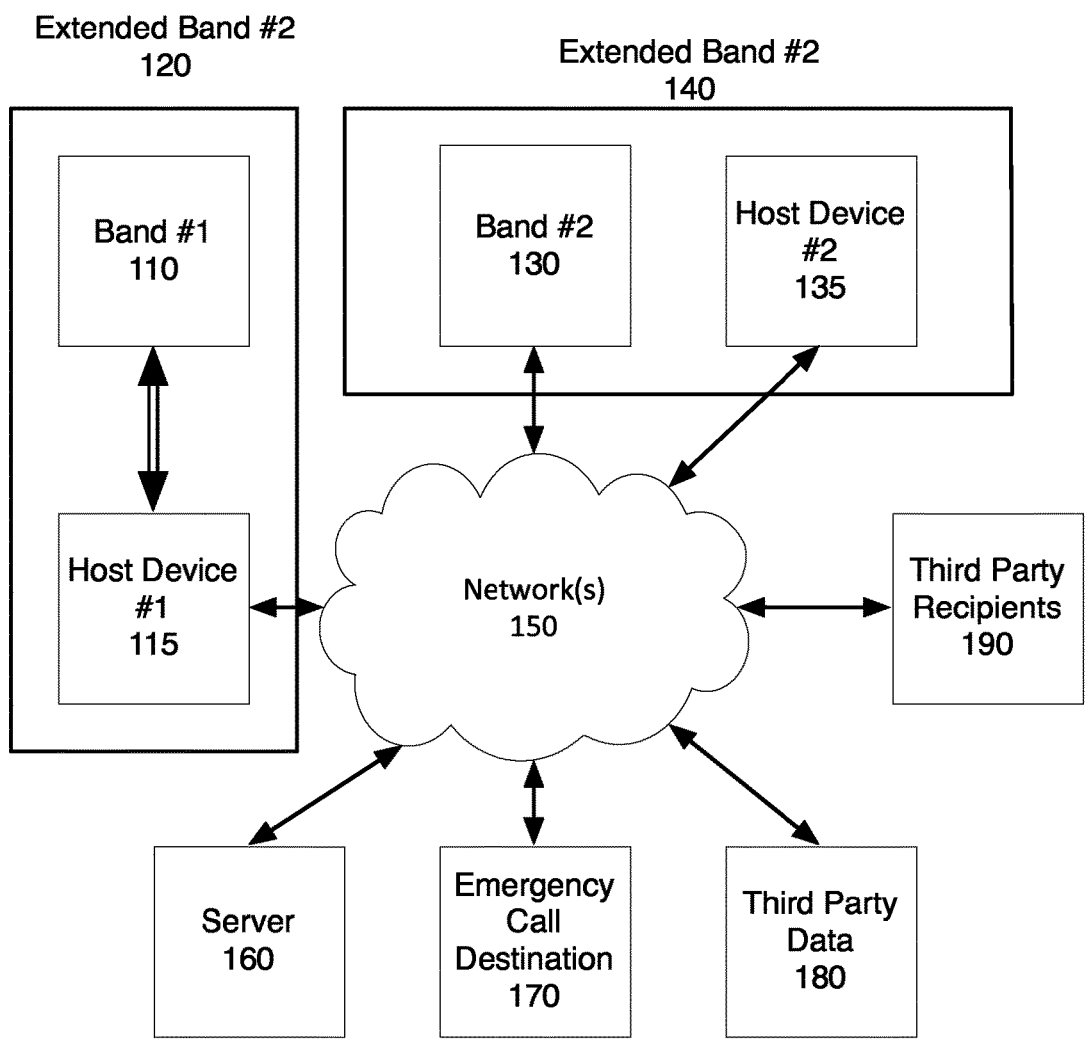
FIG. 1 is a block diagram of one embodiment of a system in which the present invention may be implemented.

The present invention is an extended band, which is a combination of a body-worn device with sensors and a computing device. The body-worn device is designed to be worn by a user throughout the day and the night, in one embodiment. In one embodiment, the extended band system includes a plurality of body-worn devices, some of which may be optimized for use during the day, and some during the night. In one embodiment, at least one sensor is worn or touched, placed next to on a soft surface, or carried by the user throughout the day. This enables the extended band to monitor the user's motions and other characteristics during the day and night. The tracking of sleep using actigraphy enables the detection of sleep phases and circadian rhythms. In one embodiment, the data obtained by the extended band may be used to track the user's activity level, create correlations between behaviors, and/or track various other health-related features, such as ergonomics, eating patterns, etc. The extended band provides useful feedback on the user's own status, and in one embodiment the status of others.

The extended band provides a MACS (Monitor, Alert, Control and Share) system. The system uses sensors on the band and/or the host device to Monitor the user's state. The system can provide Alerts on one or more component on the system, smart sleep cycle alarms, inactivity notifications, etc. The system also provides Control, enabling the user to control the band from the host device and vice-versa. The system also enables a user to Share data about themselves with others, through social media or directly with other users of the extended band system.

The body-worn device in one embodiment may be a band, such as a wristband or armband, including one or more sensors, processors, and input/output elements. For simplicity, the body-worn device will be referred to in this application as "band" though the actual configuration may include a wristband, armband, headband, necklace, glasses, chest strap, earpiece or earring, or any other configuration that is worn on the user's body. Thus, the term "band" should be interpreted to mean a body-worn device including at least one sensor and a communication mechanism enabling the body-worn device to communicate with a computing device, or incorporating the computing device. In one embodiment, the body-worn device is an activity band, as described in co-pending U.S. patent application Ser. No. 12/819,195, assigned to the same assignee, and incorporated herein by reference. An extended band may include a plurality of body-worn devices, which in one embodiment may communicate with each other, directly or through the computing device.

The computing device may be a mobile device such as a smart phone, or tablet computer, or desktop computer. The computing device may include one or more sensors, processors, and input/output elements. For simplicity, the computing device will be referred to as a host device in this Specification. Thus, the term "host device" should be interpreted as any computing device that can establish a sporadic or continuous connection with the band.

The band and host device, in one embodiment, maintain their connection most of the time that the devices are in range, thereby forming the extended band, consisting of the band(s) and related host device(s). The extended band is able to use the combination of sensors to get more accurate data, and to leverage the rich user interface of the host device (speakers, large screen, vibrations, etc.). This enables the extended band, and the system as a whole, to use the host device for real-time feedback to the user. Furthermore, sensors in the host device may add additional data to the system. Additionally, by controlling the band from the host device, the user has more fine-grained control. On the other side, by controlling the host device from the band, the system provides always-in-hand control for the host device.

For example, the band can notify the host device that it is time to wake-up the user, then an application on the host device can play sounds to wake-up the user. These sounds can gently fade-up and be user selectable. If the host device is connected to a home automation system, it can turn on lights, raise shades, start the coffee maker, etc. Because the host device is designed to be regularly charged, it can be much less power-conscious than a band designed to be worn for a longer time before recharging.

In this system, in one embodiment, the band and the host device become essentially extensions of each other, and all features of the host device can be used for real-time monitoring, alert, control, and sharing. Similar, the band may be used to provide monitoring, alerts, control, and sharing. For example if the host device is out of range (e.g. left behind), or, if the host device is a smartphone, when a call is received, the band can control the host device, or provide an alert to the user. In one embodiment, the band may be used selectively for indicating a received call, e.g. when the phone is set to silent or the user is in a loud environment. In one embodiment, elements of the band's user interface and state can be controlled from the host device. For example, the band can be put into sleep mode from the host device. Thus, the host device becomes an extension of the band and the band an extension of the host device. In one embodiment, elements of the host device's user interface and state can be controlled by the band, in turn. In one embodiment, the band may be used to turn on the host's ringer, turn on and off sensors, or otherwise control the host device.

The following detailed description of embodiments of the invention make reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

FIG. 1 is a block diagram of one embodiment of a system in which the present invention may be implemented. The system includes a band 110 and an associated host device 115. The band 110 and host device 115 make up an extended band 120. Although only one band 110 and host device 115 are shown as being associated as an extended band 120, in one embodiment, a plurality of bands may be paired with a plurality of host devices to form a single extended band. For example, the user may have a band that is a wristband for daily wear, and a different band that is designed to look nicer for special occasions, and an armband for sleeping. The host device 115 may be the user's smart phone, as well as the user's tablet, laptop, music player, and/or other device. Thus, a band may be paired to multiple hosts, and a host may be paired to multiple bands, in one embodiment. In one embodiment, if there are a plurality of hosts, the hosts communicate with each other. In one embodiment, the bands are host-agnostic. In one embodiment, when there are multiple available bands, the system determines which band is being worn by the user, and utilizes data only from that band. The determination may be made based on movement data, temperature data or other information from the band. In one embodiment, the user may also add the information. In one embodiment, the system may be capable of having more than one active band at the same time. For example, a user may wear multiple bracelet bands. In one embodiment, the system combines data from the sensors of the multiple bands in such an instance.

The extended band 120 may be coupled via a low bandwidth direct connection such as Bluetooth 4.0 or similar connection mechanism. In one embodiment, the connection between the extended band 120 and host device 125 may be continuous, periodic, or sporadic. In one embodiment, the preferred connection is continuous, enabling the use of the host device 125 as the input and output for the band 120, and enabling fine-grained control of the band. The host device 115 may be coupled to a network 150, such as the Internet. In one embodiment, the connection between a band 130 and host device 135 may be through a network 150. This configuration still forms an extended band 140.

The extended band 120, 140 may be coupled through the network 150 to a server 160. The server 160 may be a remote server or a local device that acts as a server. The server 160 may be used to collect data from multiple users/devices. In one embodiment, the network may also enable use of third party data 180, or provision of data to third parties 180. In one embodiment, the network connection may also enable the extended band 120, 140 to connect to an emergency destination 170.

In one embodiment, data from the extended band 120, 140 may be shared with various third party recipients 190. The third party recipients 190 in one embodiment may include social networks, such as FACEBOOK®, TWITTER®, GOOGLE+®, PINTREST® or other social networks, blogs, websites set up for the purpose, such as a competition site set up by NIKE® or another extended band supporter, or other third party recipients 190.

In one embodiment, an extended band 120, 140 may also share data directly with another user's extended band 120, 140. In another embodiment, data may be shared through third party recipients 190. For example, one user's post on TWITTER® or check-in on FOURSQUARE® may be received by another user's extended band 120, 140, and shared with the user through the user interface provided by host device 115, 135. As another example, the extended bands of both people may provide their data to a server, associated with supporting the extended bands. The server may share the extended band data with other users, who are associated with the owner of the extended band. This association may be voluntary (e.g., friends or connections set up by the user), circumstantial (e.g., users competing in the same competition, or being matched for an event), locational (e.g. users participating in the same race, or being in proximity), or otherwise established. In one embodiment, the bands may share data directly, without using the server 190 as the intermediary, if the users are associated.

Figure 2:
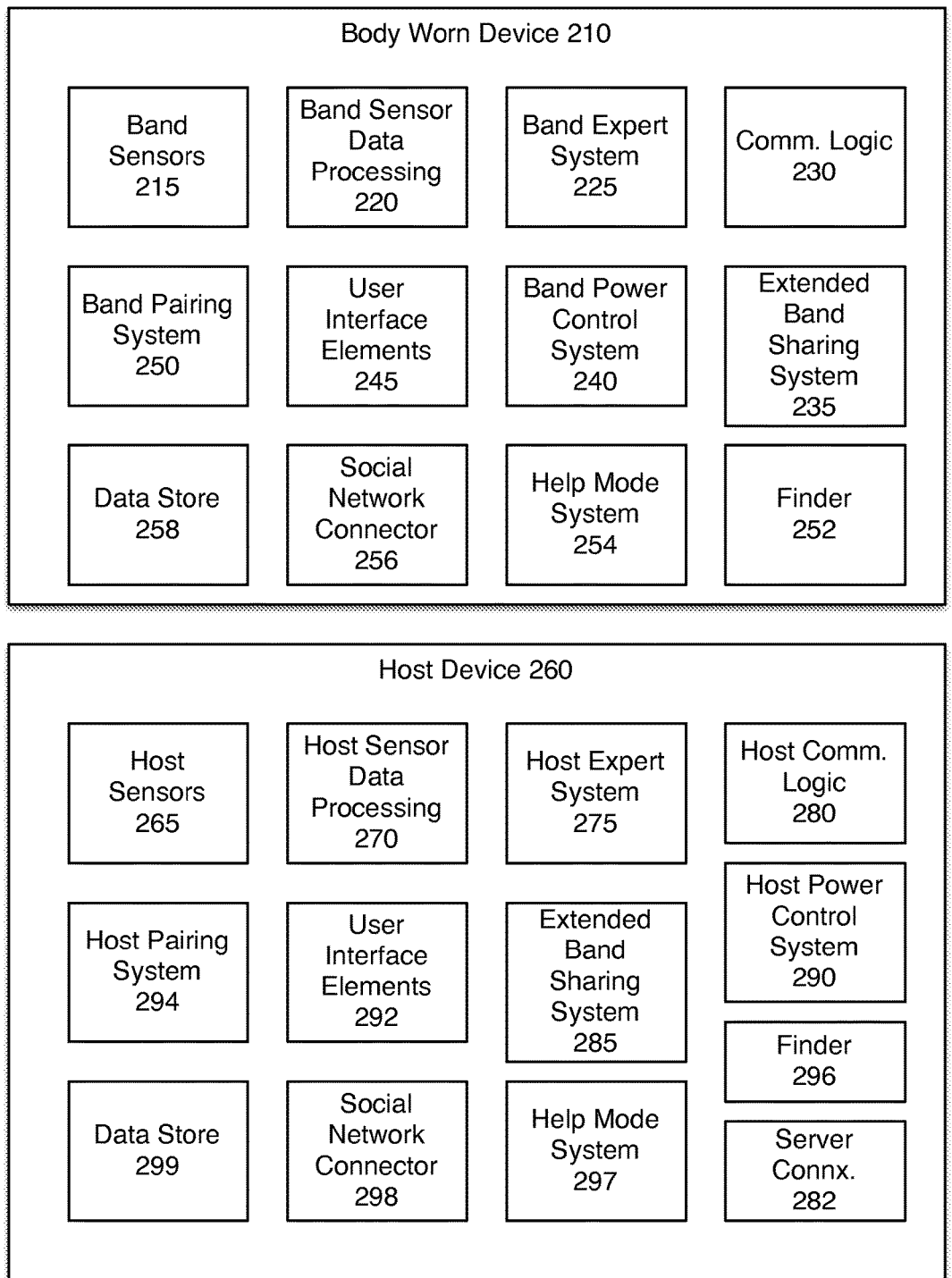
FIG. 2 is a block diagram of one embodiment of the extended band, including a body-worn device and a mobile device working together.

FIG. 2 is a block diagram of one embodiment of the extended band, including a body-worn device 210 and a host device 260 working together. Although only one body-worn device 210 or band is shown, and one host device 260 is shown, it should be understood that multiple devices 210 may work together in various ways. In the below example, each logic is reproduced in both the band 210 and the host device 260. In one embodiment, certain logics may be implemented in only one of the devices. If a logic or element exists in both devices, in one embodiment, the processing shared between the devices, and both devices can contribute data and processing power.

The body-worn device 210 includes a plurality of sensors 215. The sensors, in one embodiment, may involve sensors used to detect the user's physiological condition. Such sensors may include an accelerometer, gyroscope, thermometer (potentially two thermometers, one for ambient and one for body temperature), barometer, etc. In one embodiment, additional sensors focused on medical applications may also be included. Such sensors may include blood glucose sensors, blood pressure sensors, blood oxygenation sensors, and other sensors. In one embodiment, the sensors may be coupled to the body-worn device 210 or host device wirelessly or using a wired connection.

The sensor data, obtained by sensors 215, is passed to band sensor data processing 220. In one embodiment, the sensor data processing 220 is implemented using a processor. In one embodiment, the band sensors 215 may run off a separate lower powered processor, and store the sensor data temporarily in a buffer (not shown). In one embodiment, the higher powered processor, which implements band sensor data processing 220, may be turned on as needed. In one embodiment, the band sensor data processing 220 may also be a low power processor, and any processing requiring higher power may use the host device 260. The host sensor data processing 270 may provide additional processing power.

Band power control system 240 controls the processors of the body-worn device. In one embodiment, the power control system 240

Band expert system 225 and host expert system 275 use the processed sensor data to make recommendations and analyze the results. The expert system is designed to make recommendations.

Communication logic 230 in band and host communication logic 280 enable the close tying of the body-worn device 210 and host device 260. In one embodiment, communication logic 230 uses BLUETOOTH™ personal area network (PAN). Other network communication methods may be used. BLE (BLUETOOTH LOW ENERGY) also known as BLUETOOTH SMART may be the connection method. Other formats of network connection may be used. In one embodiment, the body-worn device may be physically coupled to the host device, continuously or periodically. The extended band sharing system on the band 235 and host 285, work together to share processing and display. In one embodiment, the band communication is limited by the user interface elements 245 available on the band, whereas in general, the host device 260 is a more fully featured, with a keyboard and LCD screen.

User interface elements 245 on band enable the user to interact with the body-worn device. In one embodiment, the band user interface elements may include buttons, keyboards, screens, or just a simple LED. The user interface elements 245 on the band in general are more limited than the user interface elements 292 in the host device 260. In one embodiment, the system is designed to provide basic communication to the user via the body-worn device 210, and provide more details upon request via the host device 260.

Band power control system 240 is used to minimize the power consumption by the body-worn device 210. The band power control system 240 reduces the power consumption of the band, by shutting off sensors that are not being utilized, reducing band power consumption when the band is not being worn, and minimizing the use of the high power processing. In one embodiment, the band power control system 240 may adjust the power consumption of the band based on the remaining power level. So, for example, the system may reduce the power consumption of the band when the battery is low, by shifting more of the processing to the host device 260. In one embodiment, the power control system is a smart system, activating the subset of sensors and processing power required on an as-needed basis.

In one embodiment, data store on the band 258 may store sensor data from band sensors 215, prior to processing. Post-processing data may also be stored in data store 258. In one embodiment, data store 258 may be a non-volatile memory, such as a flash memory. Data store 299, on host device 260 may be a non-volatile memory such as flash memory, or storage such as a disk drive.

In one embodiment, the body-worn device includes a social network connector 256, which enables the user to post directly from the band. In another embodiment, the social network connector 298 resides on the host device 260, and utilizes data from the body-worn device.

Band pairing system 250 is used to initialize a connection between the body-worn device 210 and the host device 260. In one embodiment, the pairing may use an automatic pairing, triggered by shaking the devices together or performing another activation mechanism. In one embodiment, the mechanism described in U.S. Pat. No. 7,907,901 is used.

In one embodiment, multiple body-worn devices 210 may be paired to a single host 260. This provides use flexibility and fashion. For example, a wristband that is comfortably worn during a workday may be suboptimal for exercise or sleep. Therefore, different bands may have different functionality. Additionally, different bands may have different appearances. Additionally, a single body-worn device 210 may be paired with multiple hosts 260. For example, a band may be paired with the user's mobile phone, as well as the user's tablet computer, desktop, laptop, etc. Additionally a band may be paired with a special purpose system.

Help mode system 254 enables a connection to 911 or other emergency numbers, as appropriate. In one embodiment, help mode system 254 provides an interface that enables the user to securely, quickly, and unobtrusively invoke an emergency response. In one embodiment, multiple help modes may be available, depending on the emergency. For example, a fire may be a different help mode interface than a mugger or a medical emergency. In addition to being able to call 911 or the appropriate first responders, in on embodiment, help mode system 254 may also be set to contact a family member, doctor, or other appropriate party.

Finder 252 enables the band to find the host device and vice versa. In one embodiment, the proximity system can alert the user when he or she leaves behind the body-worn device 210, or the host device 260. This can be useful especially when the user puts down the host device 260, or takes off the body-worn device 210 regularly. In this way, the extended band formed by the band 210 and host device 260 can provide an extended MACS (monitor, alert, control, share) system. The extended band provides functionality which neither the band 210 nor the host device 260 could provide alone. Additionally, by creating a truly linked band 210 and host 260, rather than occasionally sharing data, the extended band can take advantage of the combined feature set of both devices.

Figure 3:
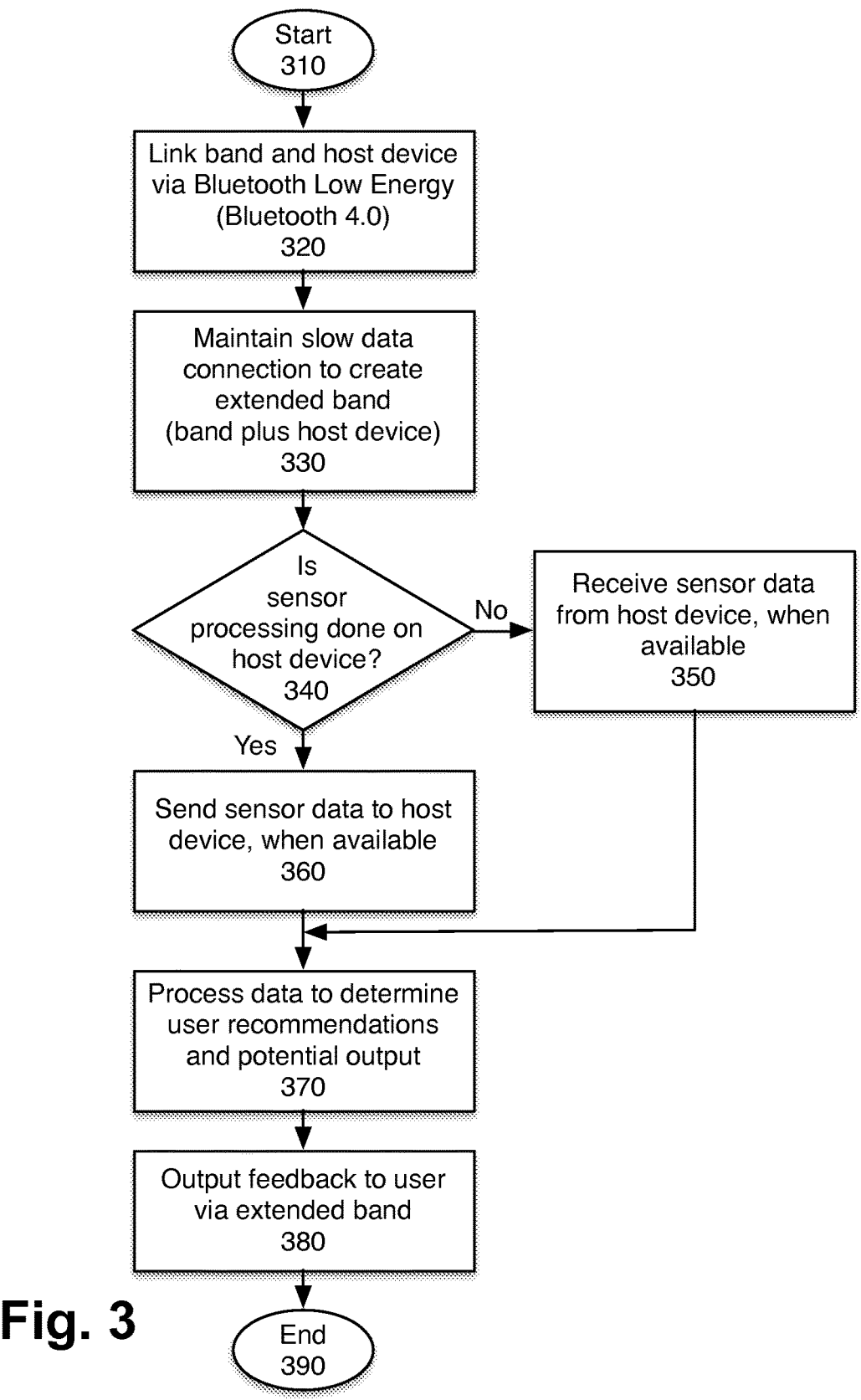
FIG. 3 is an overview flowchart of one embodiment of using the extended band.

FIG. 3 is an overview flowchart of one embodiment of using the extended band. FIG. 3 illustrates using a Bluetooth Low Energy (BLE, also known as Bluetooth 4.0) connection. Of course, other embodiments may use other wireless protocols. By preference, low power wireless protocol is used. The process starts at block 310, when the band is initially activated.

At block 320, the band and the host devices are paired via the low-power wireless protocol. In one embodiment, that protocol may be the BLE protocol. In one embodiment, pairing is done as described in FIG. 4 below.

At block 330, a slow and low-power data connection is maintained between the band and the host device, to create the extended band. The extended band is a combination of the sensors, processors, input and output mechanisms of the band and the host device. The combination can provide better quality data, faster processing, and a richer output than either device alone.

At block 340, the process determines whether sensor data processing is done by the host device, the band, or a combination. In one embodiment, if both the host device and the band can do processing, the processing will be distributed as is most efficient. In one embodiment, the decision may be made based on processor capability, available battery power, bandwidth cost, and sensor data volume. In one embodiment, the host device has a more powerful processor but the band has more sensors. In one embodiment, pre-processed sensor data is shared, rather than raw data.

The process determines whether the processing is being done on the host device, at block 340. If the processing is not done on the host device, at block 350, sensor data is received by the band from the host device. If the processing is done on the host device, at block 360, sensor data is sent to the host device by the band. In one embodiment, each device may do some pre-processing on its sensor data, before sharing it. Preprocessing data removes unnecessary data. For example, for a motion sensor, the accelerometer output is a change in acceleration at all times. The pre-processed data may remove portions that contain no movement. In one embodiment, the pre-processed data, for an accelerometer, may provide an acceleration vector showing direction, strength, and length of movement, rather than raw accelerometer data. In one embodiment, each device may process its sensor data separately.

At block 370, the data is processed to determine user recommendations and outputs. In one embodiment, the outputs may be alarms, reminders, status indicators, status updates updates, etc. In one embodiment, feedback is output to the user at block 380. The feedback may additionally be shared on social networks, or pushed to other users of the application, in one embodiment. The process ends at block 390. In one embodiment, the connection is maintained when the devices are both powered and available, and thus this process ends only when one of the two devices is disconnected or turned off.

Figure 4:
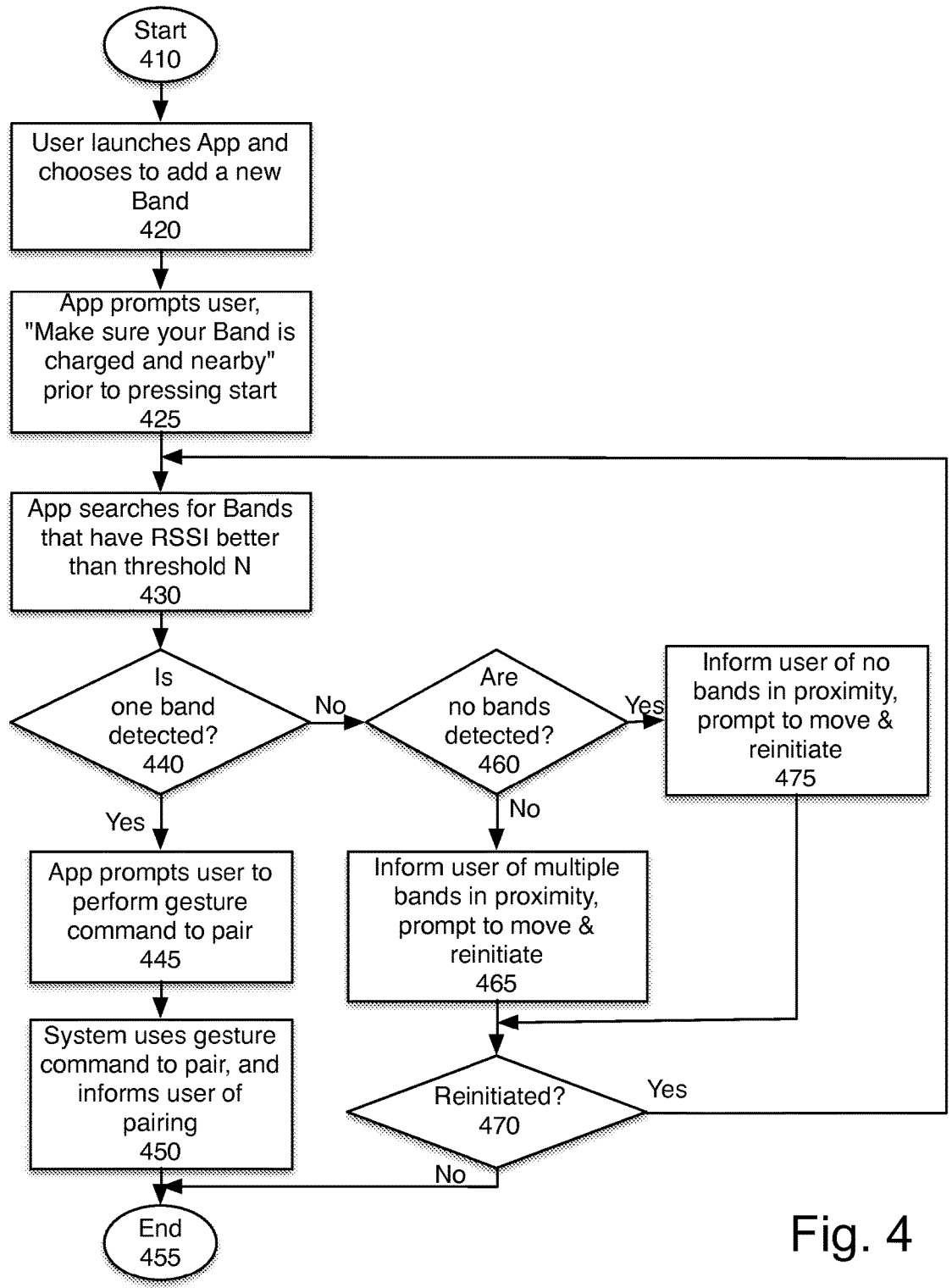
FIG. 4 is a flowchart of one embodiment of pairing the mobile device and the band.

FIG. 4 is a flowchart of one embodiment of pairing the mobile device and the band. This describes the initial pairing of a new band to a host device. In one embodiment, this flowchart corresponds to block 320 of FIG. 3. The host device runs an application (app), which is used to provide the input/output for the extended band. The process starts at block 410.

At block 420, the user launches the application, and chooses the option to add a new band. In one embodiment, this may be done from a configuration menu or the like in the application. In one embodiment, this may be done using a hardware button or similar mechanism.

At block 425, the application prompts the user to make sure the band is charged and nearby, prior to pressing start. The start button may be a soft button or a hard button. In another embodiment, the start button may be a gesture command or other initiation mechanism.

At block 430, the application searches for a band that has a received signal strength indicator (RSSI) greater than a threshold.

At block 440, the process determines whether a single band is detected. If so, at block 445, the application prompts the user to perform a gesture command to complete the pairing. This ensures that the band whose signature was detected is the band being paired. The gesture command, in one embodiment, is holding the host device and the band together and performing a motion. In another embodiment, a sequence of key presses or other interaction with the band may be used instead to complete the pairing. In another embodiment, the band ID (which may be a name, a color, or another identification) is displayed and the user can accept the pairing. In one embodiment, the user may need to accept the pairing on both the band and the host device in one embodiment, to ensure that an unrelated host device can't be paired with a band.

At block 450, the gesture command is used to pair the host device and band. In one embodiment, the process described in U.S. Pat. No. 7,907,901, assigned to the assignee of the present invention, may be used to perform the pairing. The user is informed of the pairing. The process then ends at block 455.

If at block 440 the system did not detect a single band, the process continued to block 460. At block 460, the process determines whether no bands were detected. If no bands were detected at block 475 the user is informed that no bands were successfully detected, and the user is prompted to ensure that the band to be paired is charged and in proximity to the host device. The process then continues to block 470, enabling the user to reinitiate the pairing. If the user reinitiates the pairing, the process returns to block 430, to search for bands in proximity with an RSSI above a threshold. If the pairing is not reinitiated, the process ends.

If, at block 460 multiple bands were found, in one embodiment, the process continues to block 465. At block 465 the user is warned that multiple bands were found in proximity, and prompted to move, with the one band to pair and the host device, or alternatively to remove the other bands from the vicinity, or turn them off. The process then continues to block 470, enabling the user to reinitiate the pairing. In another embodiment, the user may simultaneously pair multiple bands with the host device. In that case, the process continues to block 445 when the one or more bands are detected.

In this way, the system enables establishing the pairing between the host device and the band. Once a host device and a band are paired, forming the extended band, whenever the two devices are in proximity they automatically establish a connection. Additionally, as described above, the extended band utilizes the combined sensor set and processing power of the band and the host device.

Figure 5:
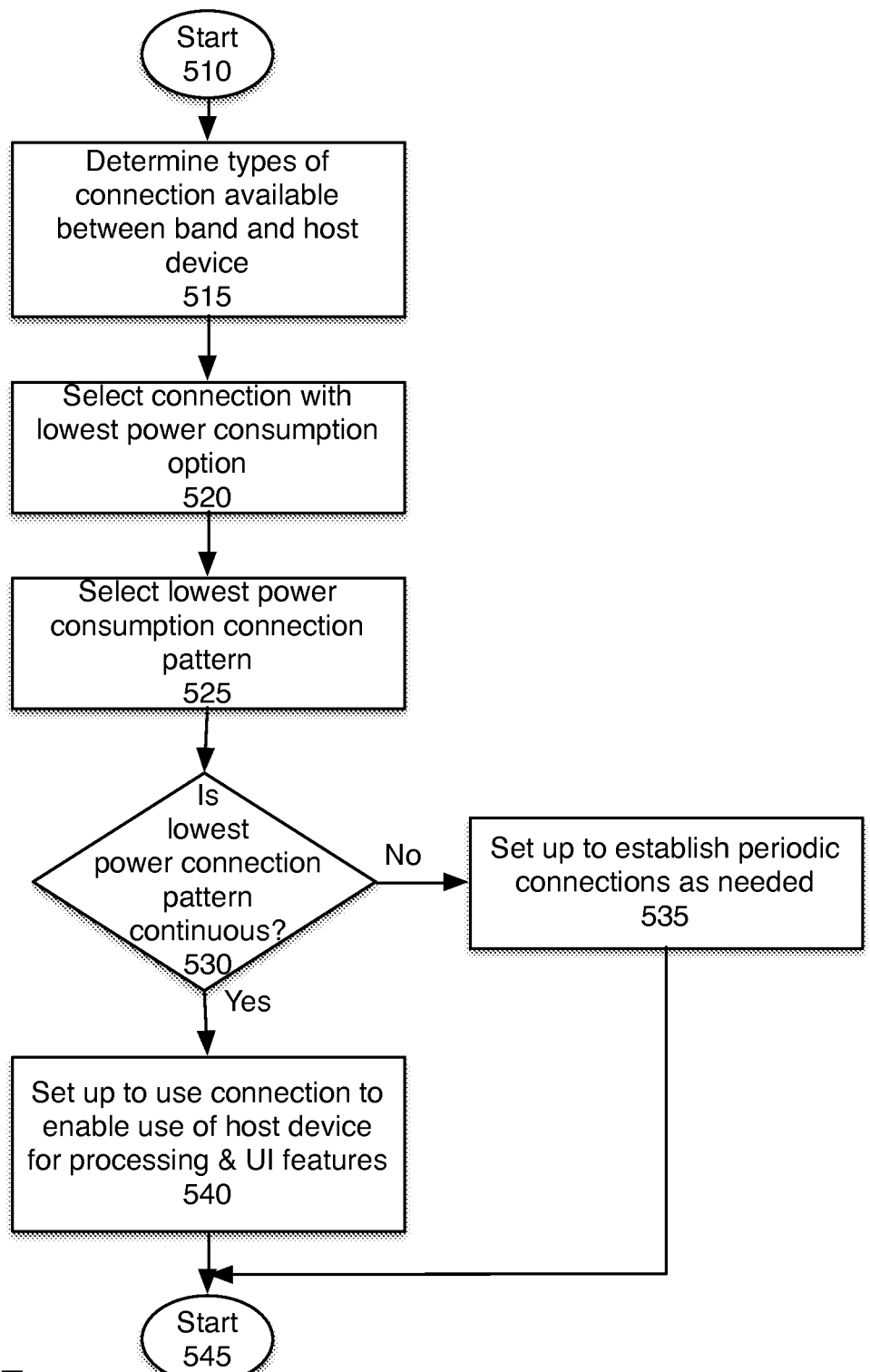
FIG. 5 is a flowchart of one embodiment of selecting a connection method between the mobile device and the band.

FIG. 5 is a flowchart of one embodiment of selecting a connection method between the mobile device and the band. In one embodiment, bands may be connected to various host devices such as a smartphones, special purpose mobile devices, tablet computers, mini tablets, laptop computers, desktop computers, or other devices. These various host devices may have different capabilities, in terms of types of wireless connectivity. The types of wireless connectivity may include various types of wireless personal area networks (WPAN), local area networks (LAN), 802.11-type networks, and other types of connections.

At block 515, the types of connections available between the band and host devices are identified. The types of connections include all connection formats that are supported by both the host device and the band.

At block 520, the lowest power connection that can support the data exchange between the band and host device is selected. In general, the goal is to have a band that needs to be recharged once or twice a week, or at a minimum no more frequently than every 24 hours. Because the band is designed to monitor motion, sleep, and ergonomics, it is designed to be worn continuously. Therefore, long battery life is strongly preferred.

At block 525, a connection pattern that is the lowest consumption is selected. Depending on the type of connection, the lowest consumption pattern may be a continuous connection sending small amounts of data (Bluetooth 4.0) or periodic connections to send high bandwidth bursts of data. In one embodiment, based on the connection method selected, the lowest power connection pattern is selected.

At block 530, the process determines whether the selected connection pattern is continuous. As noted above, for some connection formats, a continuous low power connection is preferred. If so, at block 540, the system is set up to use a continuous connection, at block 540. In one embodiment, the continuous connection exchanges data in a low bandwidth format regularly. If not, at block 535 the system sets up timing for periodic connections, or sets up a pattern of establishing connections as needed. The process then ends.

Figure 6:
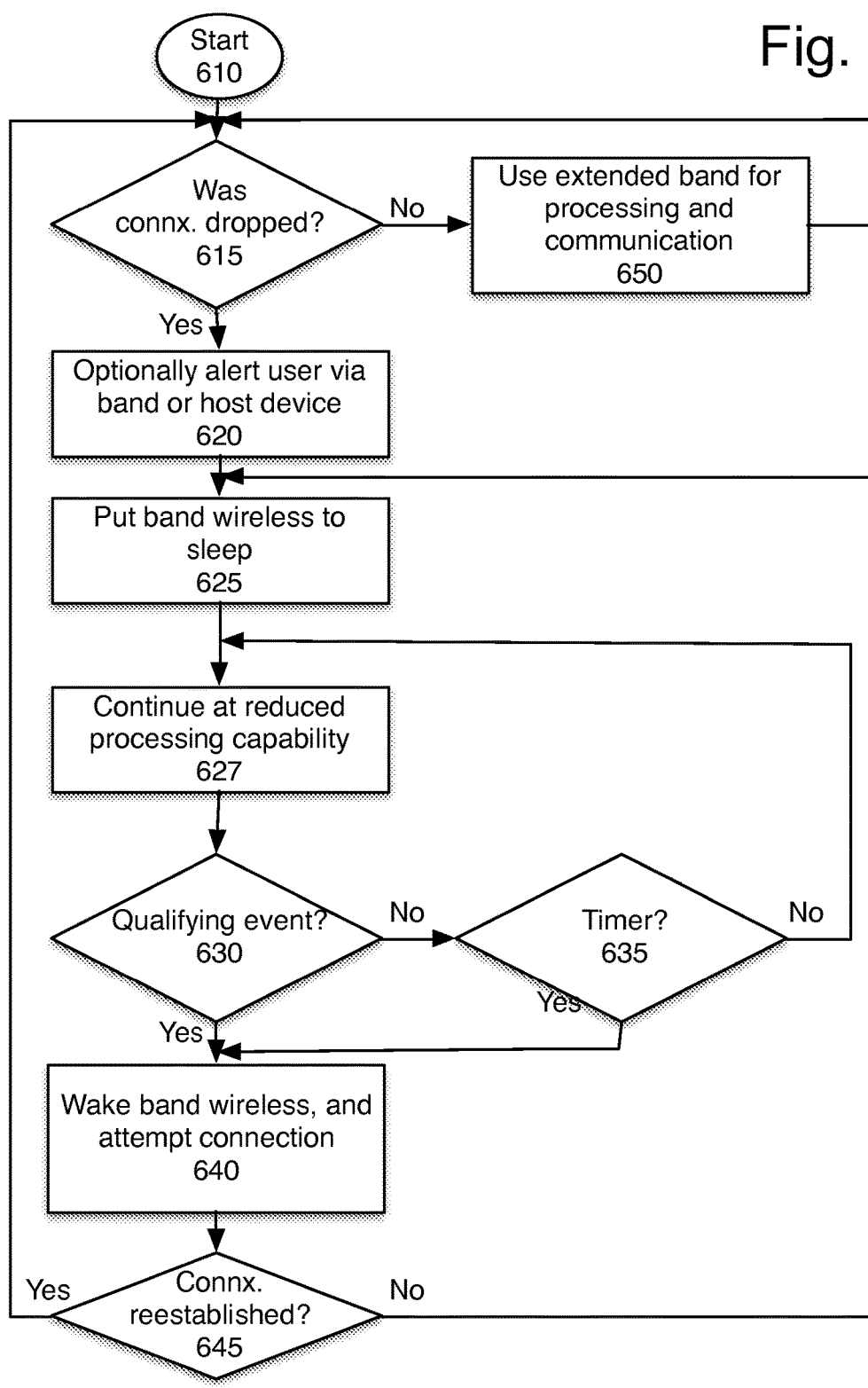
FIG. 6 is a flowchart of one embodiment of handling lost connections in the extended band.

FIG. 6 is a flowchart of one embodiment of handling lost connections in the extended band. In one embodiment, the extended band assumes that that connection between the band and the host device is on-going, either continuously or on a periodic basis. When the systems cannot connect, in one embodiment, the following process is used. The process starts at block 610. In one embodiment, this process is continuously running, when the extended band is in use.

At block 615, the process determines whether the connection was dropped. A dropped connection occurs if an attempt to share data between the band and the host device fails. In one embodiment, at least a plurality of attempts must fail, to declare a connection dropped. In one embodiment, if three attempts fail, the connection is deemed dropped.

If the connection has not dropped, at block 650 the combination of band and host device is used to acquire sensor data, process it, and communicate with the user. Additionally the extended band may share data with third parties including social networks, as well as present data to the user from third parties including social networks. The process continues back to block 615, to continue utilizing the extended band and monitoring for a dropped connection.

If the connection was dropped, at block 620 the user is alerted via the band and/or host device, in one embodiment. The alert may be useful to indicate that the band or host device was left behind accidentally, has been turned off, or has developed a problem. In one embodiment, the alert on the band may be a vibration or light, while the host device may use an alarm tone and a display on its screen. Other methods of alerting the user may be used. In one embodiment, a text or MMS message may be generated to alert the user.

At block 625 the band's wireless connection is put to sleep. As noted above, the band's battery should be maintained. Wireless connectivity is one of the significant battery drains, and especially attempts to connect wirelessly uses a lot of signal strength and thus battery. Therefore, temporarily placing the band's wireless connection in a sleep state is a way of preserving battery power.

At block 627, the other processes of the band are continued, at a reduced level. In one embodiment, if the band cannot process some of the sensor data, it stores and queues the data to be sent to the host device. From the user's perspective, in one embodiment, the band's functionality does not significantly change, unless the band cannot support the required processing. In that case, the system attempts to continue functioning with the reduced processing power, prioritizing user-relevant actions. For example, if the user is sleeping and awaiting an alarm, the band would continue to monitor sleep and ensure that the alarm was not missed. Other processes may be queued for later processing. The band also queues other communications that would normally take place with the host device, e.g. user status updates and processed sensor data.

At block 630, the process determines whether a qualifying event has taken place. A qualifying event may include the user pressing a button on the band, ending a sleep or timed steps recording, the band detecting that it is time to wake-up the user (smart sleep alarm), etc. If a qualifying event is detected, at block 640 the band's wireless connection is woken, and the band should attempt to connect to the host device again. At block 645, the process determines whether the connection was reestablished. If not, the process continues to block 625, and puts the wireless connection back to sleep. Of course, the band would also perform the actions triggered by the qualifying event. If the connection is successfully reestablished, the band sends the data previously queued to the host device, and the process returns to block 615 to continue interacting with the host device and monitor the status of the connection.

If no qualifying event took place, at block 630, at block 635 the process determines if a timer has triggered. If the time set by the timer has not passed, the process returns to block 627, to continue reduced service, and determine whether a qualifying event has been detected. If the timer has been triggered, at block 640 the band wireless is woken, and a connection is attempted. In this way, the almost continuous connection between the band and the host device is maintained, while optimizing for reduced power consumption by the band and user-relevant processing when processing is limited to the band. Although this figure shows the dropped connection from the perspective of the band, one of skill in the art would understand that the host device uses a similar process. When the sensor data, and other information from the band is not available, the host device continues to process what data it has available, and attempts to keep the user experience consistent. In one embodiment, if the system is being used for sleep monitoring, the host device may change to a user-modified sleep pattern, and still wake the user using a smart alarm. This is designed to ensure that if the band runs out of power, or crashes, or otherwise becomes inactive, the user still has a positive experience with the system.

Figure 7:
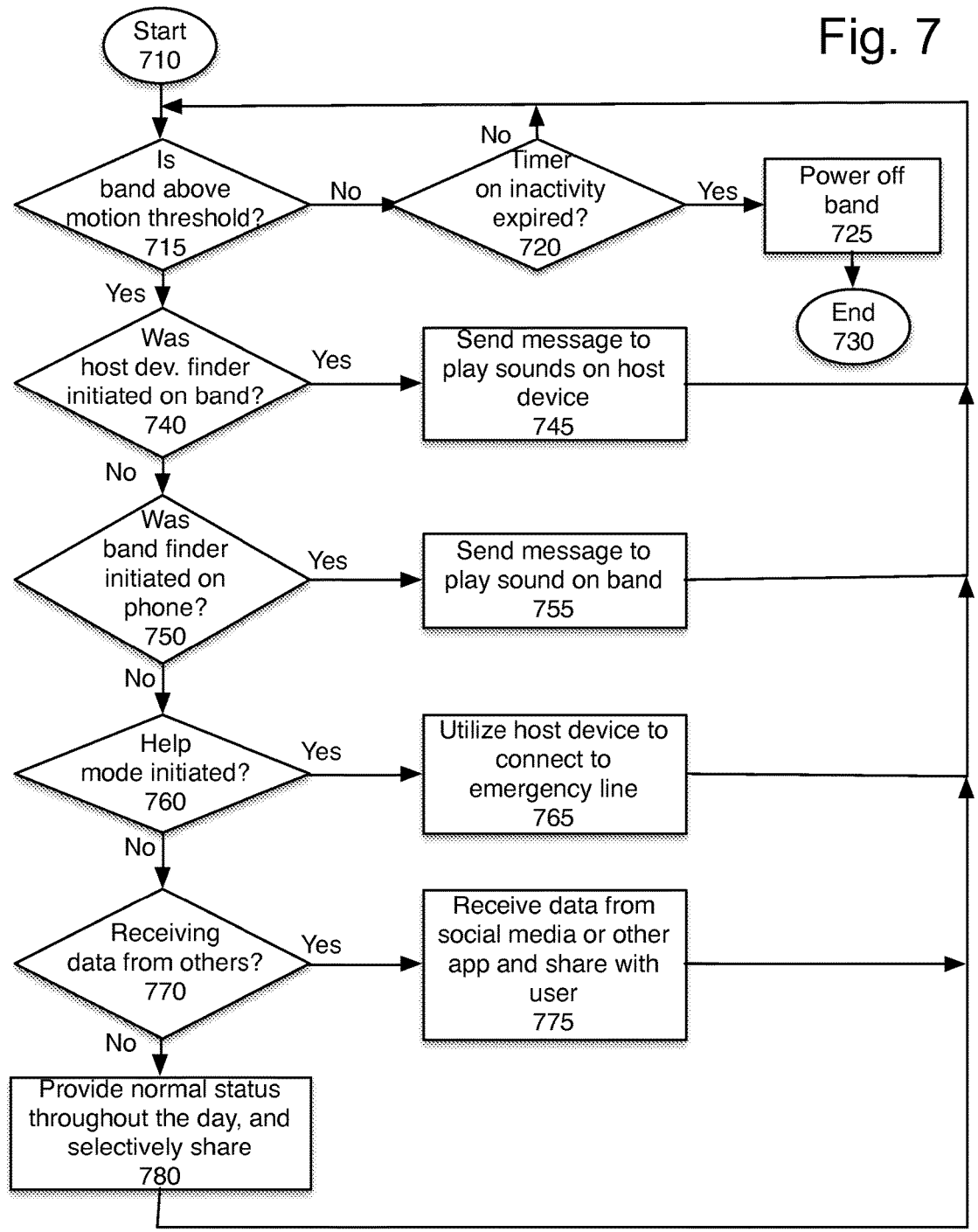
FIG. 7 is a flowchart of one embodiment of using the extended band.

FIG. 7 is a flowchart of one embodiment of using the extended band. The process starts at block 710. At block 715, the process determines whether the band is above a motion threshold. This determination attempts to identify whether the band is being worn, or not. Even when not moving a human body exhibits certain motions, such as tremors and a rhythmic movement caused by the heart beating. The motion threshold is set, in one embodiment, to be able to use the involuntary motions to determine that the band is in use. If the band is below the motion threshold, at block 720 the process determines whether the band has been inactive for a period of time. If so, at block 725, the band is powered off. The process then ends at block 730. In one embodiment, the band sets a timer, and periodically checks if there is movement above a threshold. In another embodiment, the user should manually turn on the band after it is powered off. If the band has not been inactive for a period, the process returns to block 715, to continue monitoring whether the band motion level is above the threshold.

If the band's motion is above the threshold, as determined at block 715, the process continues to block 740. At block 740, the process determines whether host device finder was initiated on the band. In one embodiment, when the user is wearing the band and cannot find his or her host device, which is a mobile device, he or she may activate this feature. If it was activated, at block 745 a message is sent to trigger an action on the host device. In one embodiment, the message is sent through the application that may be able to override a silent setting. This enables the user to locate the host device, if the host device has any power. In one embodiment, the output is played repeatedly until the user indicates that the band is found. In one embodiment, if the band and host device are not in close enough proximity to use the personal area network such as BLUETOOTH, another network protocol may be used for this message. The process then returns to block 715.

If the host device finder is not activated, the process determines whether the band device finder is activated, at block 750. If so, at block 755, a message to use the band output is sent from the host device to the band. The output may be a sound, a vibration, a flashing light, or a combination of those or any other forms of output that the band can utilize. In one embodiment, the output is played repeatedly until the user indicates that the band is found. In one embodiment, if the band and host device are not in close enough proximity to use the personal area network such as BLUETOOTH, another network protocol may be used for this message. In one embodiment, if the host device has the capability to determine the location of the band, the system may also provide an indication of the approximate direction of the band. The process then returns to block 715.

If the band finder was not initiated, at block 760, the process determines whether a help mode is initiated. The help mode may be initiated by pressing and holding a button, squeezing the band, or another indication. In one embodiment, this indication is designed to not be accidentally triggered, and easy enough to enable someone who is hurt to perform the indication.

In one embodiment, the user may utilize the band to initiate a help mode. The help mode connects the user to an emergency number, such as 911 or a pre-programmed third party such as a doctor or monitoring service, using a combination of the band and the host device. This would enable a user who is unable to reach or dial a telephone to call for help. If the help mode is initiated, at block 765, the system uses the extended band to connect to the emergency line. In one embodiment, the combination of the host device and the band enables a user to talk to the emergency number responder (such as a dispatcher) without having to dial and hold a telephone. In one embodiment, there may be multiple types of help modes that may be triggered. For example, there may be a "medical emergency" trigger, a "non-medical emergency" trigger, and a "dangerous situation" trigger. In one embodiment, the user may define one or more triggers, and one or more destinations. In one embodiment, the default help mode initiation is to contact 911 or the equivalent local emergency service.

In one embodiment, help mode may be initiated automatically, e.g. without a user triggering it, in some circumstances. For example, in one embodiment, if the band sensors detect that the user is having a medical emergency, help mode may be initiated. For example, if the band can monitor heart rate automatically, a heart rate in the danger zone (e.g. heart arrhythmia or heart racing without a corresponding movement trigger) may automatically trigger the help mode. In one embodiment, the user is provided with the opportunity to override the help mode trigger, if it is automatically initiated. In one embodiment, the ability to terminate the help mode is also provided when it is manually triggered, enabling the user to override it. The process then returns to block 715 to continue monitoring.

If no help mode was initiated, the process at block 770 determines whether the system has received data from other users. In one embodiment, the user may set up one or more "friends" with whom the user wishes to share data, and whose data the user wishes to see. If one of those friends has sent data, at block 775 the data is received and shared with the user. In one embodiment, the system includes a page that displays the user's own status and the status of friends. The data received may include social media posts, such as posts on FACEBOOK®, or TWITTER® or another social media platform. The data received may include data directly shared between instances of the application, e.g. each user may set up to share certain milestones achieved, such as how much and how well the user slept, how much aerobic activity the user did, how many steps the user took, etc. In one embodiment, the received data is a combination of these types of data. In one embodiment, the user may be alerted to certain social media data, based on user-set preferences. The process then returns to block 715 to continue monitoring.

If no data is received, at block 780, the system provides normal user status to the user throughout the day. The user interface, generally made available on the host device, is continuously updated so that it is up-to-date with the user's latest activity and sleep data. It is designed so that the user can glance at the application and see how he or she is doing today. In one embodiment, by incorporating the shared data received from others, the user can also see how he or she is doing relative to personal activity/sleep goals and relative to other people/friends in their social network.

In one embodiment, the band also provides some of this feedback throughout the day. In one embodiment, the band has a screen (display), which allows for feedback/status updates throughout the day. In one embodiment, the user's current status may be reflected by an LED or other illustrating showing a relative status (e.g. green when the user has met his or her goals, shading into yellow as they slip, and red when the user is far from his or her set goals. Alternatively, the user's relative standing among his or her friends may be indicated via display on the band. For example, the user in first place among the friends may have a gold light, while the second has silver, third bronze, and others different colors. This enables an at-a-glance comparison between friends. In one embodiment, a competition logic, described for example in U.S. patent application Ser. No. 11/740,884, assigned to the assignee of this case, may be used to enable competition between unevenly matched users.

In one embodiment, in addition to providing data to the user, the process also enables the user to selectively share the user's status with friends. As noted above, the application may share certain achievements and status. In one embodiment, the user sets up what information is shared with whom, and once the preferences are set, the extended band automatically shares data. In one embodiment, the user may also manually share data, or block data from being shared. The process then returns to block 715 to continue monitoring.

In this way, the extended band, utilizing the band and the paired host device provide services to the user. Additional services may be provided, with sensor data, sensor data processing, data sharing, and notifications utilizing the band, the host device, or both devices. By providing an extended band that is linked consistently with the host device, the user has the advantages of both form factors, and the disadvantages of neither.

FIG. 8 is a flowchart of one embodiment of optimizing the sharing or processing and display on the extended band. The process starts at block 810. In one embodiment, this process is continuous when the extended band is in use.

At block 815, the process determines whether there is user output to be provided. The system provides alerts, alarms, and other types of notifications to the user. In one embodiment, does not include updates to the user's information presented on the band or host device, as discussed with respect to FIG. 7.

If there is user output to be provided, the system at block 820 identifies the optimal combination of outputs based on the type of connection between the host and band, power levels of the host and band, and host and band capabilities. In one embodiment, the system preferentially outputs user alerts and data through the host device, since the host device provides a richer experience. In one embodiment, the relative location of the host device and band may also be taken into account, e.g. if the user is wearing the band but the host device is not nearby, the band may be a better output mechanism. In one embodiment, the distance between the host and band may be determined based on connection latency. In one embodiment, if one of the devices has low power, the system preferentially uses the other device in the extended band to provide feedback to the user. FIG. 9 illustrates some exemplary methods of providing output to the user. Once the optimal combination of the outputs is determined, at block 825 the output is provided to the user. The process then returns to block 815 to continue monitoring.

If there is no output to be provided, the process determines whether there is data to be processed. The data to be processed may include sensor data such as motion data, heart rate data, or other types of data. The data to be processed may also include third party data. In one embodiment, data processing includes not only using raw sensor data to determine the user's activities, sleep phase, ergonomics, etc., but also providing trend analysis and other processing. If there is data to be processed, at block 835 the process identifies the ideal combination of the band and host device, and optionally a remote system such as a server, to process the data. In one embodiment, this too may be based on the capabilities, power levels, and data sets available to the devices. The process at block 840 then determines whether the data needs to be passed from its current source for processing. If not, the processing takes place and the process returns to block 815 to continue monitoring.

If at block 840 the process determines that the data needs to be passed, at block 845 the data is passed from the band to the host device/server, or from the host device to the band/server, as determined. The data is then processed. In one embodiment, if the other device will use the data, in one embodiment the processed data is passed back at block 850. In another embodiment, the result of the processing is passed back. In one embodiment, a relevant output or change in settings or state based on the data is passed back. In another embodiment, nod data is returned. The process then returns to block 815 to continue monitoring.

If there is no data to be processed, at block 855 the process determines whether there is sensor data to be shared. If so, at block 860 the sensor data is received. The sensor data may be received by the band from the host device, or by the host device from the band. The process then returns to block 815 to continue monitoring.

If there is no sensor data to be shared, the process continues to block 865. At block 865, the process determines whether the band or host device is low on power. If a band or host device is low on power, in one embodiment, the system attempts to reduce the likelihood that it will run out of power entirely, by reducing the demands made by the extended band on the low-battery device.

If a device is low on power, at block 875 the processing and output is shifted to the other device. At block 880, the inessential elements of the device are turned off. For example, if the band is low on power, in one embodiment, all sensors except the motion sensor may be turned off. In one embodiment, if the host device has an available motion sensor and is being carried, the motion sensor may also be turned off. In normal use, when power levels are not an issue, the host device and the band may both monitor user motions, to provide a more detailed picture of the user's activities. However, when a power issue comes up, the elements not absolutely necessary may be turned off, to extended battery power. If there is no power issue, the process continues directly to block 815. In one embodiment, the system may minimize power consumption even when there is not a low power issue. In that case, only one carried device would monitor movement and other physiological data, and only one device outputs information to the user. This is less accurate than having two sets of data, but is more power efficient. In one embodiment, the trade-off level may be set by the user.

Figure 10:
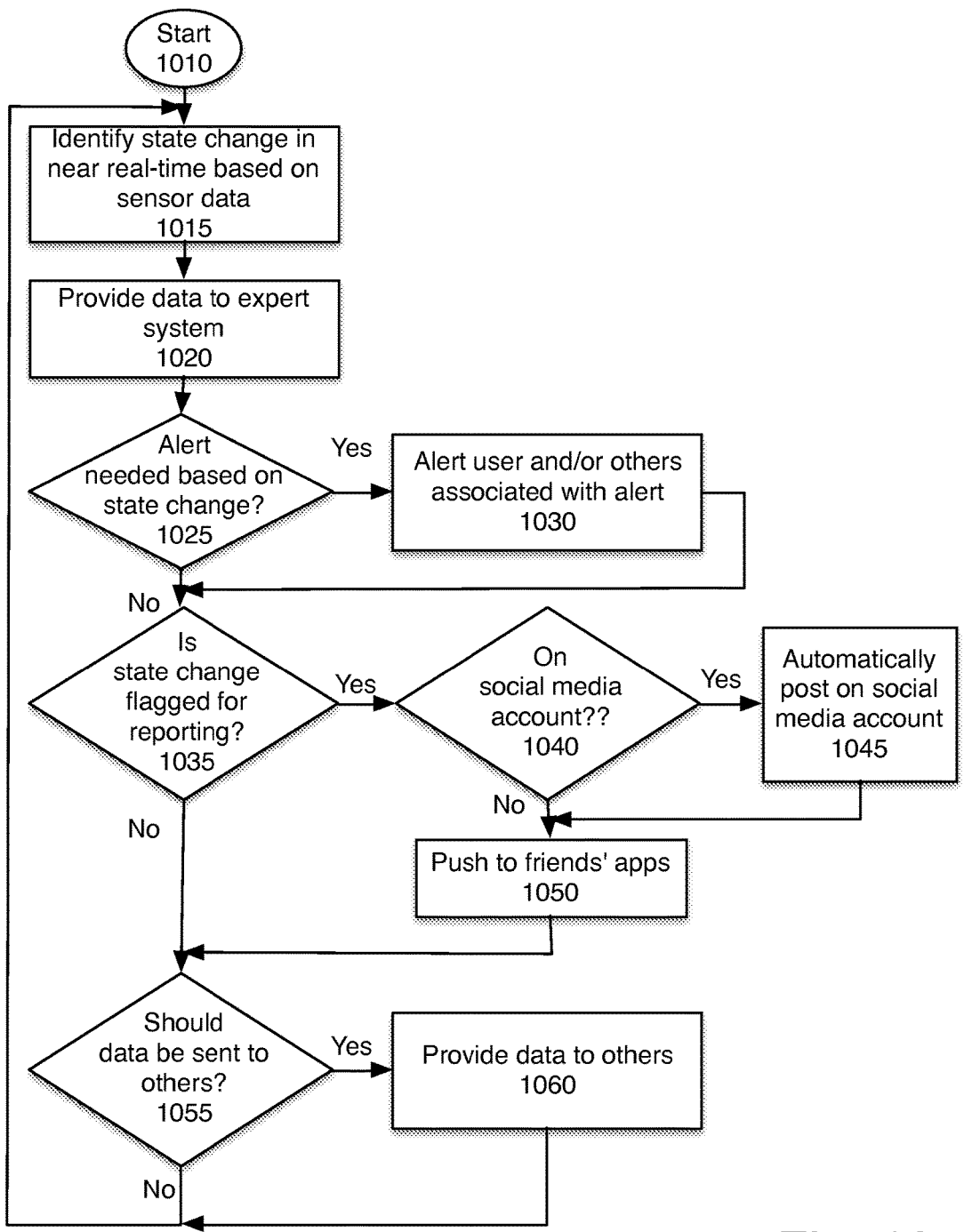
FIG. 10 is a flowchart of one embodiment of information sharing using the extended band.

FIG. 10 is a flowchart of one embodiment of information sharing using the extended band. The process starts at block 1010. In one embodiment, this process monitors data and information sharing whenever the extended band is in use.

At block 1015, a state change is identified in near real-time based on sensor data. State changes may include the user starting or stopping an activity, starting or stopping a sleep session, meeting a goal, having an ergonomic issue, etc.

At block 1020, the data is provided to an expert system. The expert system may be on the band, the host device, or on both the band and host device. The expert system analyzes the data and data trends, to determine whether the state changes, and history of this user, indicates an issue. An issue is anything that should be shared with the user. An issue may be "you should stand up, you have been sitting too long," or "you need to start going to bed earlier," or something similar that is not urgent but useful to know. On the other hand, an issue may be a health problem, such as a stroke, heart attack, or indications of a flu or similar urgent health problem. It may also be an alert regarding a goal or appointment.

At block 1025, the process determines whether an alert is needed based on the state change, as determined by expert system. If so, at block 1030 an alert is sent. The alert may be sent to the user, other indicated individuals, and optionally if needed to medical or emergency personnel. The alert may be an short message system (SMS), a multimedia message system (MMS), a telephone message, an email, or another format. In one embodiment, the alert provides location data for the user, as well as the relevant information that triggered the alert. The process then continues to block 1035.

At block 1035, the process determines whether this particular identified state change is flagged for reporting. In one embodiment, state changes are flagged for reporting by the user. For example, the user may set the rule that after waking, the system should post his or her sleep data "e.g. Arthur slept for 6.25 hours, with a 98% efficiency." If the state change is flagged for reporting, at block 1040 the process determines whether it should be posted on the user's social media account, e.g. FACEBOOK®, TWITTER®, or the like. If the system determines it should be posted on a social media account, at block 1045 the application automatically posts the state change, in an appropriate format on the user's social media account.

The process then continues to block 1050. If the user has not set the state change for posting to the social media account(s), the process at block 1050 pushes the data to the user's friends' applications. In one embodiment, instead of, or in addition to, posting information on a social media account, the information may be directly provided to friends who use the same application. This is a more private way to share. In one embodiment, for friends who are selected for sharing but don't have the application available, the data may be shared through another means, such as SMS, MMS, email, etc.

The process, at block 1055 determines whether the data should be send to any other destinations. In one embodiment, these other destinations may include a server collecting statistical data, other data recipients such as doctors treating the user, etc. If so, at block 1060, the data is provided to others in whatever format is specified. In one embodiment, the data may be provided in formats ranging from short messaging service (SMS), multimedia messaging (MMS), email, fax, or other formats. The process then returns to block 1015 to continue monitoring for state changes.

Although the communication methods discussed in FIG. 10 are triggered by state change, the state change may simply be a particular time of day, or a calendar event, or some other trigger. There is no need for a "state change" to be a significant event, in one embodiment.

Figure 11:
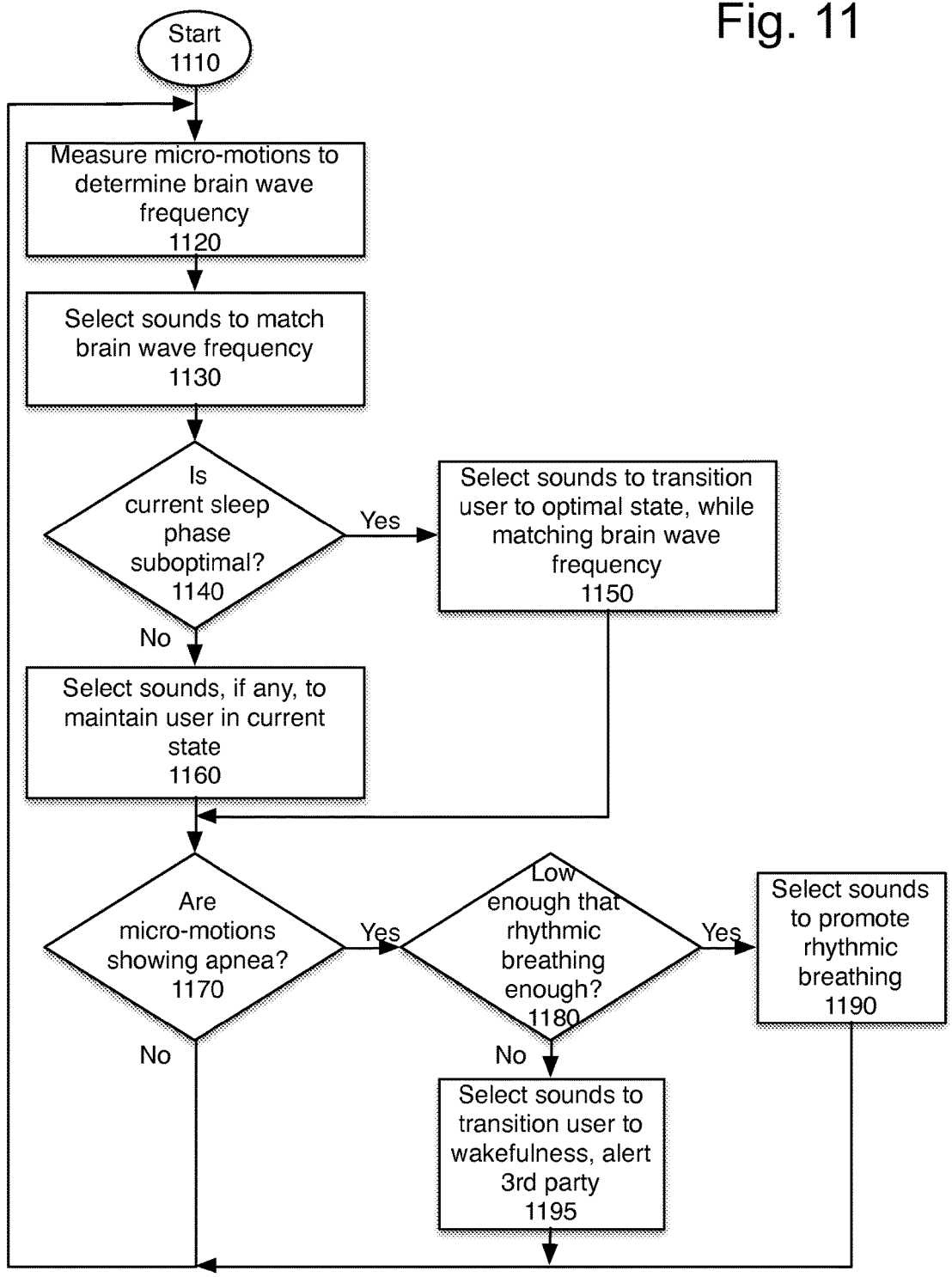
FIG. 11 is a flowchart of one embodiment of sleep monitoring using the extended band.

FIG. 11 is a flowchart of one embodiment of sleep monitoring using the extended band. In one embodiment, this may be implemented with the band or the host device alone, as well. The process starts at block 1110. In one embodiment, this process starts when the user initiates asleep session. The sleep session may be initiated manually or the system may automatically detect when the user falls asleep.

At block 1120, the process measures micro-motions to determine the user's brain wave activity and brain wave frequency, in one embodiment. In one embodiment, the brain wave activity may also be detected based on other sensor data. In one embodiment, the user's heart rate may also be monitored.

At block 1130, the system selects sounds to match brain wave frequency. At block 1140, the process determines whether the user's current sleep phase or sleep quality is suboptimal. In one embodiment, the sleep phase is determined based on the micro-motions and brain wave activity.

If the user is in the wrong sleep phase, at block 1150 the system selects sounds to transition the user to a more optimal sleep phase. In one embodiment, the sounds also match brain wave frequency. If the current sleep phase is not suboptimal, at block 1160, in on embodiment the system selects sounds to maintain user in the current sleep phase and improve sleep quality. In one embodiment the system does so while matching brain wave frequency.

At block 1170, the process determines whether the micro-motions are showing sleep apnea. If not, the process returns to block 1120 to continue monitoring the user's sleep.

If the micro-motions, and optionally other data, indicate sleep apnea, the process at block 1180 determines whether rhythmic breathing would be sufficient to move the user out of the apnea state. Sleep apnea occurs when someone is not breathing properly, often because part of their throat is obstructed. Sometimes, simply prompting them with sounds triggering deeper breaths is sufficient. In one embodiment, at block 1190 sounds are selected to promote rhythmic deeper breathing. In one embodiment, the sounds also match brain wave frequency associated with a deep breathing stage. This feedback is designed to move the user from the shallow infrequent breaths of apnea into the deeper and healthier breathing state.

If the apnea is too severe for that, at block 1195 the system selects sounds to transition the user to wakefulness. In one embodiment, the system may also alert a third party, such as the user's spouse or doctor, of the apnea. The process then returns to block 1110 to continue monitoring. In one embodiment, the process ends when the user's sleep session is terminated.

In one embodiment, the system may similarly monitor for other unhealthy sleep behaviors, such as snoring, teeth grinding, restless leg, and other behaviors or symptoms that would make the user's sleep quality or quality of life worse. In one embodiment, the system attempts to transition the user into a different sleep phase when these unhealthy behaviors are detected. In one embodiment, the user is also informed, after he or she wakes up. In one embodiment, suggestions for additional treatment may also be provided to the user. Thus, in one embodiment, the user's sleep summary includes descriptions of detected unhealthy behaviors, and suggestions on how to reduce their impact in the future. In one embodiment, the expert system correlates the unhealthy behaviors with other behaviors of the user during the preceding day or other time period. For example, the system may determine that the user snores when he or she ate a late meal. The user may be alerted to this correlation, hopefully causing a change in behavior and thus an overall healthier user.

One of ordinary skill in the art will recognize that the processes described in the above flowcharts are conceptual representations of the operations used. The specific operations of the processes may not be performed in the order shown and described. For example and in one embodiment, the process is interrupt driven, rather than sequentially testing for various occurrences. In one embodiment, data is received or processed in a different order. The specific operations may not be performed in one continuous series of operations, and different specific operations may be performed in different embodiments. Additional operations may be performed, or some operations may be skipped. Furthermore, the processes could be implemented using several sub-processes, or as part of a larger macro process. For instance, in some embodiments, the processes shown in these flowcharts are performed by one or more software applications that execute on one or more computers.

Figure 12:
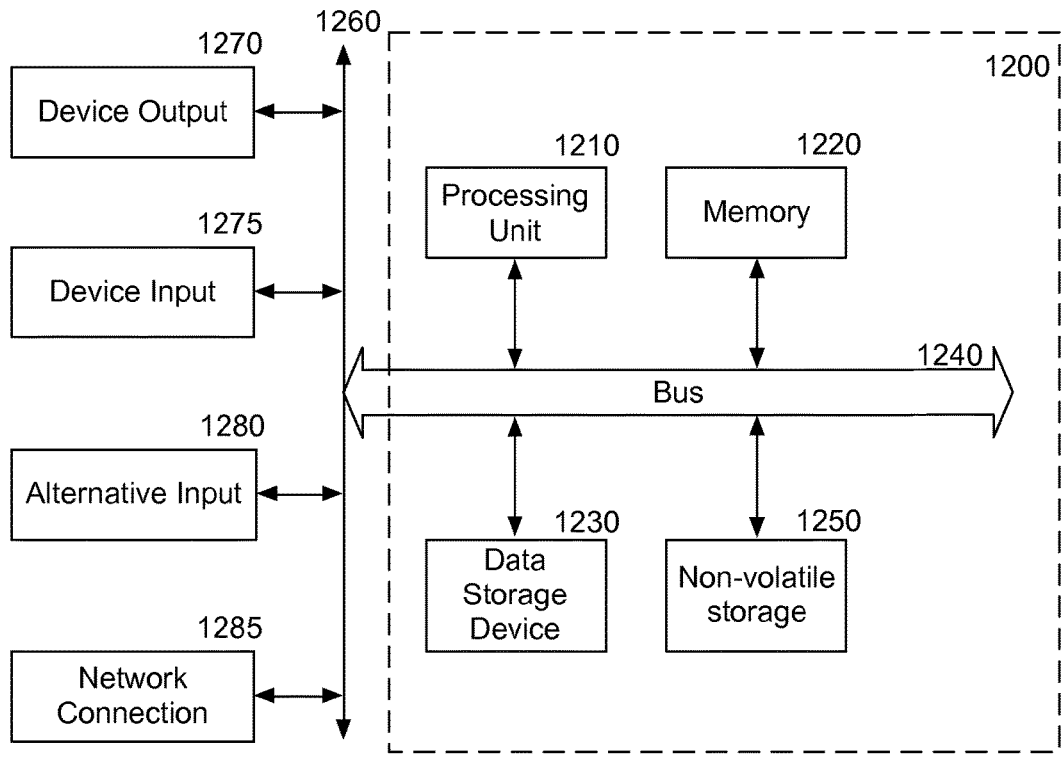
FIG. 12 is a block diagram of one embodiment of a computer system that may be part of the present invention.

FIG. 12 is a block diagram of one embodiment of a computer system that may be part of the present invention. FIG. 12 is a block diagram of a particular machine that may be used with the present invention. It will be apparent to those of ordinary skill in the art, however that other alternative systems of various system architectures may also be used.

The data processing system illustrated in FIG. 12 includes a bus or other internal communication means 1240 for communicating information, and a processing unit 1210 coupled to the bus 1240 for processing information. The processing unit 1210 may be a central processing unit (CPU), a digital signal processor (DSP), or another type of processing unit 1210.

The system further includes, in one embodiment, a random access memory (RAM) or other volatile storage device 1220 (referred to as memory), coupled to bus 1240 for storing information and instructions to be executed by processor 1210. Main memory 1220 may also be used for storing temporary variables or other intermediate information during execution of instructions by processing unit 1210.

The system also comprises in one embodiment a read only memory (ROM) 1250 and/or static storage device 1250 coupled to bus 1240 for storing static information and instructions for processor 1210. In one embodiment the system also includes a data storage device 1230 such as a magnetic disk or optical disk and its corresponding disk drive, or Flash memory or other storage which is capable of storing data when no power is supplied to the system. Data storage device 1230 in one embodiment is coupled to bus 1240 for storing information and instructions.

The system may further be coupled to an output device 1270, such as a cathode ray tube (CRT) or a liquid crystal display (LCD) coupled to bus 1240 through bus 1260 for outputting information. The output device 1270 may be a visual output device, an audio output device, and/or tactile output device (e.g. vibrations, etc.)

An input device 1275 may be coupled to the bus 1260. The input device 1275 may be an alphanumeric input device, such as a keyboard including alphanumeric and other keys, for enabling a user to communicate information and command selections to processing unit 1210. An additional user input device 1280 may further be included. One such user input device 1280 is cursor control device 1280, such as a mouse, a trackball, stylus, cursor direction keys, or touch screen, may be coupled to bus 1240 through bus 1260 for communicating direction information and command selections to processing unit 1210, and for controlling movement on display device 1270.

Another device, which may optionally be coupled to computer system 1200, is a network device 1285 for accessing other nodes of a distributed system via a network. The communication device 1285 may include any of a number of commercially available networking peripheral devices such as those used for coupling to an Ethernet, token ring, Internet, or wide area network, personal area network, wireless network or other method of accessing other devices. The communication device 1285 may further be a null-modem connection, or any other mechanism that provides connectivity between the computer system 1200 and the outside world.

Note that any or all of the components of this system illustrated in FIG. 12 and associated hardware may be used in various embodiments of the present invention.

In one embodiment, the band may include a subset of these elements, such as a processor, flash memory, input/output mechanism, and communications mechanism. The host device may include a subset of superset of these elements, but at least a processing device and a communication device.

It will be appreciated by those of ordinary skill in the art that the particular machine that embodies the present invention may be configured in various ways according to the particular implementation. The control logic or software implementing the present invention can be stored in main memory 1220, mass storage device 1230, or other storage medium locally or remotely accessible to processor 1210.

It will be apparent to those of ordinary skill in the art that the system, method, and process described herein can be implemented as software stored in main memory 1220 or read only memory 1250 and executed by processor 1210. This control logic or software may also be resident on an article of manufacture comprising a computer readable medium having computer readable program code embodied therein and being readable by the mass storage device 1230 and for causing the processor 1210 to operate in accordance with the methods and teachings herein.

The present invention may also be embodied in a handheld or portable device containing a subset of the computer hardware components described above. For example, the handheld device may be configured to contain only the bus 1240, the processor 1210, and memory 1250 and/or 1220.

The handheld device may be configured to include a set of buttons or input signaling components with which a user may select from a set of available options. These could be considered input device #1 1275 or input device #2 1280. The handheld device may also be configured to include an output device 1270 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 1210, a data storage device 1230, a bus 1240, and memory 1220, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 1285.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 1210. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In one embodiment, the host device is computer system with the expert system and analysis performed by a processor, DSP, or similar processing-capable device. In one embodiment, the host and/or band may include multiple processors, such as a low power processor and a high power processor. In one embodiment, the sensors may be separately powered as well.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. An extended band system comprising:
 a body-worn device including at least one sensor and a communication mechanism;

a host device paired with the body-worn device, the host device and the body-worn device maintaining a continuous low-bandwidth connection;
a plurality of sensors, implemented in the body-worn device and/or the host device;
the extended band system providing an improved monitoring of the user's states and a rich feedback mechanism;
each of the host device and the body-worn device provide for a plurality of user input, processing of the user's states, and user output; and
the extended band selecting one or both of the host device and the body-worn device to provide the user input, the processing, and the user output, based on status factors of the host device and the body-worn device, the status factors consisting of at least two of sensor data volume, connection cost, connection quality, richness of output, and power level.

2. The extended band system of claim 1 further comprising:
a pairing system to pair the body-worn device and the host device; and
a communication logic to establish a low-power connection between the body-worn device and the host device to enable sharing of data between the host device and the body-worn device.

3. The extended band system of claim 2, wherein the communication logic is further to determine one or more types of connections supported by both the body-worn device and the host device, select a lowest power consumption connection type, and identify a lowest power consumption connection pattern, based on the connection type chosen;
wherein the connection between the body-worn device and the host device uses the lowest power consumption connection type and the lowest power consumption connection pattern.

4. The extended band system of claim 1, further comprising:
an extended band sharing system to share sensor data between the body-worn device and the host device; and
sensor processing system to analyze the sensor data to determine the user's state and identify user state changes.

5. The extended band of claim 1, further comprising:
a communication logic to determine when the continuous low-bandwidth connection between the body-worn device and the host device is dropped; and
a band power control system temporarily turning off the communication mechanism of the band when the connection is dropped, to save power.

6. The extended band of claim 5, further comprising:
the band power control system further to turn on the communication logic when a qualifying event happens, the qualifying event comprising one or more of: a timer expiring, a notification to the user being generated, a status change detected; and
the communication logic to attempt to reestablish the connection between the body-worn device and the host device.

7. The extended band of claim 1, further comprising:
a finder to trigger an alert on one of the devices in the extended band, from the other device in the extended band to enable finding a misplaced device.

8. The extended band of claim 1, further comprising:
a help mode system to automatically connect the user to an emergency line, when help mode is invoked, the help mode using a combination of the body-worn device and the host device to enable the user to communicate with the emergency line.

9. The extended band of claim 1, further comprising:
a social network connector to automatically share status updates, the sharing comprising sending the status updates to one or more of: a social media network of the user, a friend of the user who also has the application, and a third party.

10. The extended band system of claim 1, wherein the status factors consist of all of: sensor data volume, connection cost, connection quality, richness of output, and power level.

11. A method of providing an extended band comprising:
pairing a body-worn device and a host device;
establishing a low-power connection between the body-worn device and the host device;
monitoring a user's status with a plurality of sensors;
determining that data should be presented to the user, based on the user's status;
determining one or both of the body-worn device and the host device to use to output the data to the user;
providing for a plurality of user input, processing of the user's states, and user output through each of the host device and the body-worn device; and
selecting one or both of the host device and the body-worn device to provide the user input, the processing, and the user output, based on status factors of the host device and the body-worn device, the status factors consisting of at least two of sensor data volume, connection cost, connection quality, richness of output, and power level.

12. The method of claim 11, wherein the plurality of sensors are located in the body-worn device, the method further comprising:
sharing the sensor data with the host device; and
analyzing the sensor data to determine a user's state and identify user state changes.

13. The method of claim 11, further comprising:
determining one or more types of connections supported by both the body-worn device and the host device; and
selecting a lowest power consumption connection type; and
identifying a lowest power consumption connection pattern, based on the connection type chosen;
wherein the connection between the body-worn device and the host device uses the lowest power consumption connection type and the lowest power consumption connection pattern.

14. The method of claim 11, further comprising:
determining when a connection between the body-worn device and the host device is dropped; and
temporarily turning off the communication system of the band when the connection is dropped, to save power.

15. The method of claim 14, further comprising:
turning on the communication system when a qualifying event happens, the qualifying event comprising one or more of: a timer expiring, a notification to the user being generated, a status change detected; and
attempting to reestablish the connection between the body-worn device and the host device.

16. The method of claim 11, further comprising:
triggering an alert on one of the devices in the extended band, from the other device in the extended band to enable finding the misplaced device.

17. The method of claim 11, further comprising:
enabling the triggering of a help mode, the help mode automatically connecting the user to an emergency line, the help mode using a combination of the body-worn device and the host device to enable the user to communicate with the emergency line.

18. The method of claim 11, further comprising:
automatically sharing status updates, the sharing comprising sending the status updates to one or more of: a social media network of the user, a friend of the user who also has the application, and a third party.

19. A system comprising:
a communication logic, to link a body-worn device and a host device to create an extended band including the body-worn device and the host device;
a plurality of sensors in the extended band to monitor a user's state;
a sensor data processing logic to process the data from the plurality of sensors, the sensor data processing implemented in a processor;
user interface elements in the extended band to provide information to the user;
the extended band enabling the sensors, the data processing, and the user interface elements to be located in the body-worn device and/or the host device,
each of the host device and the body-worn device providing for a plurality of the data processing and the user output elements;
and selecting an appropriate portion of the extended band for user input, processing, and user output, based on status factors of the body-worn device and the host device, the status factors consisting of at least two of sensor data volume, connection cost, connection quality, richness of output, and power level.

20. An extended band comprising:
a body-worn device including a communication logic;
a host device including a communication logic, such that the host device is linked to the body-worn device using a low-power connection forming the extended band;
the host device and the body-worn device together providing capability to monitor a user's state, alert a user to relevant data, share data with third parties;
the extended band selecting one or both of the host device and the body-worn device to monitor the user's state, alert the user to relevant data, share data with third parties, based on status factors of the host device and the body-worn device; and
the host device configured to control settings of the body-worn device, and the body-worn device configured to control settings of the host device, the status factors consisting of at least two of sensor data volume, connection cost, connection quality, richness of output, and power level.

21. The extended band of claim 20, further comprising:
a plurality of sensors to monitor the user's state, the plurality of sensors comprising at least one sensor on the body-worn device and one sensor on the host device.

\* \* \* \* \*